(12) United States Patent
Ustuner (10) Patent No.: US 7,914,548 B2
(45) Date of Patent: Mar. 29, 2011

(54) PREVENTION OR TREATMENT OF MALE PATTERN BALDNESS METHOD AND DEVICE

(76) Inventor: E. Tuncay Ustuner, Mountain View, CA (US)

( * ) Notice: Subject to any disclaimer, the term of this patent is extended or adjusted under 35 U.S.C. 154(b) by 620 days.

(21) Appl. No.: 11/627,238

(22) Filed: Jan. 25, 2007

(65) Prior Publication Data

US 2007/0243153 A1 Oct. 18, 2007

Related U.S. Application Data

(60) Provisional application No. 60/792,497, filed on Apr. 17, 2006.

(51) Int. Cl.
*A61F 2/10* (2006.01)
(52) U.S. Cl. ...................................................... 606/187
(58) Field of Classification Search .................. 606/187, 606/280, 281, 283–285; 623/15.11, 15.12, 623/23.72, 23.74; 132/201; 128/897–899
See application file for complete search history.

(56) References Cited

U.S. PATENT DOCUMENTS

| 4,919,664 A | | 4/1990 | Oliver et al. | |
| 5,340,579 A | | 8/1994 | Casero | |
| 5,480,889 A | | 1/1996 | Goldman | |
| 5,578,599 A | | 11/1996 | Diani et al. | |
| 5,607,477 A | * | 3/1997 | Schindler et al. | 623/23.72 |
| 5,814,048 A | * | 9/1998 | Morgan | 606/283 |
| 5,877,160 A | | 3/1999 | Harper et al. | |
| 5,958,384 A | | 9/1999 | Holick | |
| 6,497,719 B2 | | 12/2002 | Pearl et al. | |
| 6,936,044 B2 | | 8/2005 | McDaniel | |
| 2004/0068284 A1 | * | 4/2004 | Barrows | 606/187 |
| 2004/0171693 A1 | | 9/2004 | Gan et al. | |
| 2005/0118282 A1 | | 6/2005 | Castor | |
| 2006/0039896 A1 | | 2/2006 | Kleinsek et al. | |
| 2007/0128172 A1 | | 6/2007 | Yoshizato et al. | |

FOREIGN PATENT DOCUMENTS

WO WO 2005/053763 6/2008

OTHER PUBLICATIONS

Jeffrey S. Epstein, et al., "Scalp Flaps in the Treatment of Baldness", Dermatologic Surgery, Inc., Jan. 1996, 22 (1); pp. 45-50.
Boris E. Goldman, et al., "Transcutaneous PO2 of the Scalp in Male Pattern Baldness: A New Piece to the Puzzle", Plast. Recons. Surgery May 1996, vol. 97, No. 6, pp. 1109-1116, discussion 1117.
Per Klemp, et al., "Subcutaneous Blood Flow in Early Male Pattern Baldness", J. of Invest. Dermatol., May 1989, vol. 92, No. 5, pp. 725-726.
Peter H. Proctor, "Hair-Raising. The Latest News on Male-Pattern Baldness", Adv. Nurse Pract., Apr. 1, 1999, vol. 7, No. 4, pp. 39-42 & 83.
Edoardo Raposio, et al., "Serial Scalp Reductions: A Biomechanical Approach", Dermatol. Surgery, Mar. 1999, vol. 25, No. 3, pp. 210-214.

(Continued)

*Primary Examiner* — Tan-Uyen (Jackie) T Ho
*Assistant Examiner* — Ryan J Severson
(74) *Attorney, Agent, or Firm* — Lempia Summerfield Katz LLC (57) ABSTRACT

Method and devices for the prevention or treatment of hair loss, particularly male pattern baldness (MPB), are provided. The pressure on the hair follicles is reduced.

24 Claims, 9 Drawing Sheets

OTHER PUBLICATIONS

Alfredo Rebora, "Pathogenesis of androgenetic alopecia", J. Am. Acd. Dermatol., May 2004, vol. 50, No. 5, pp. 777-779.

D. Stough, et al., "Psychological Effect, Pathophysiology, and Management of Androgenetic Alopecia in Men", Mayo Clinic Proc., Oct. 2005, vol. 80, No. 10, pp. 1316-1322.

Shoji Toshitani, et al., "A New Apparatus for Hair Regrowth in Male-Pattern Baldness", J. of Dermatol., Apr. 1990, vol. 17, No. 4, pp. 240-246.

James W. Young, et al., "Cutaneousimmunopathology of androgenic alopecia", J. Am. Osteopath Asso., Aug. 1991, vol. 91, No. 8, pp. 765-771.

S.I. Foote, "Hair Growth and the Fluid Factor", Medical Hypotheses (1995) 44, pp. 475-478.

PCT International Search Report and Written Opinion dated Sep. 24, 2008.

Bertucci, et al., "Hair Transplantation Update", J. of Cutaneous Med. and Surgery, vol. 2, No. 3, 1998, pp. 180-186.

* cited by examiner

PREVENTION OR TREATMENT OF MALE PATTERN BALDNESS METHOD AND DEVICE

RELATED APPLICATIONS

The present patent document claims the benefit of the filing date under 35 U.S.C. §119(e) of Provisional U.S. Patent Application Ser. No. 60/792,497, filed Apr. 17, 2006, which is hereby incorporated by reference.

BACKGROUND

The present embodiments relate to prevention and treatment of hair loss, particularly male pattern baldness (MPB).

Dihydrotestosterone (DHT) is almost universally assumed to be the major factor in the etiology of MPB. The presence of a genetic predisposition for MPB is also accepted by the most. Autoimmune mechanisms, tissue hypoxia, and scalp tension have all been suggested in the pathogenesis of MPB.

In MPB treatment, 5-alpha-reductase inhibitors to prevent conversion of testosterone to DHT and vasodilators to improve circulation have been used either alone or together (see U.S. Patent Application No. 20050118282, U.S. Pat. No. 5,578,599, and U.S. Pat. No. 5,480,889). Pharmacotherapy has also included application of various compositions that have been asserted to stimulate hair growth, such as the ones that contain creatine compound (see U.S. Patent Application No. 20040171693), emu oil (see U.S. Pat. No. 5,958,384), or hyaluronic acid (see U.S. Pat. No. 5,340,579). Finasteride and minoxidil have been approved by the Food and Drug Administration for the treatment of MPB. However, these techniques may have limited effectiveness and/or require constant treatment.

There are approaches that are more sophisticated, such as injection of cultured follicular cells (see U.S. Pat. No. 4,919,664) or follicle progenitor cells (see U.S. Patent Application No. 20040068284), or use of antisense oligomers (see U.S. Pat. No. 5,877,160). Other approaches include application of electromagnetic radiation (see U.S. Pat. No. 6,936,044), application of a laser (see U.S. Pat. No. 6,497,719), and an external apparatus that pushes up the scalp when applied (see Toshitani, et al. A New Apparatus for Hair Growth in Malepattern Baldness. J Dermatol. 1990 April, 17(4):240-6). However, these approaches may have limited effectiveness.

Surgical techniques include scalp reduction, hair transplantation, or scalp flaps. These surgical techniques redistribute available healthy hair to cover bald areas, but the results may be less than desirable.

BRIEF SUMMARY

By way of introduction, the preferred embodiments described below include methods and devices for the prevention or treatment of hair loss, particularly male pattern baldness (MPB). The pressure on the hair follicles is reduced.

In a first aspect, a device is provided for prevention or treatment of hair loss. An implant is inserted in the scalp. The implant is operable to reduce pressure on hair follicles.

In a second aspect, a method is provided for prevention or treatment of hair loss. Material is implanted in a scalp. The material is positioned to reduce pressure on hair follicles. The pressure on the hair follicles of the scalp is reduced with the material.

In a third aspect, a method is provided for prevention or treatment of hair loss. A composition of matter is obtained. The composition of matter is inserted adjacent to hair follicles at a position. The position and the composition of matter are operable to reduce gravitational pressure on the hair follicles.

In a fourth aspect, a device is operable to prevent or treat hair loss. A connection portion is operable to connect with tissue. A support portion is operable to support hair follicles with reduced pressure on the hair follicles from gravitational force against the bone.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Figure 1:
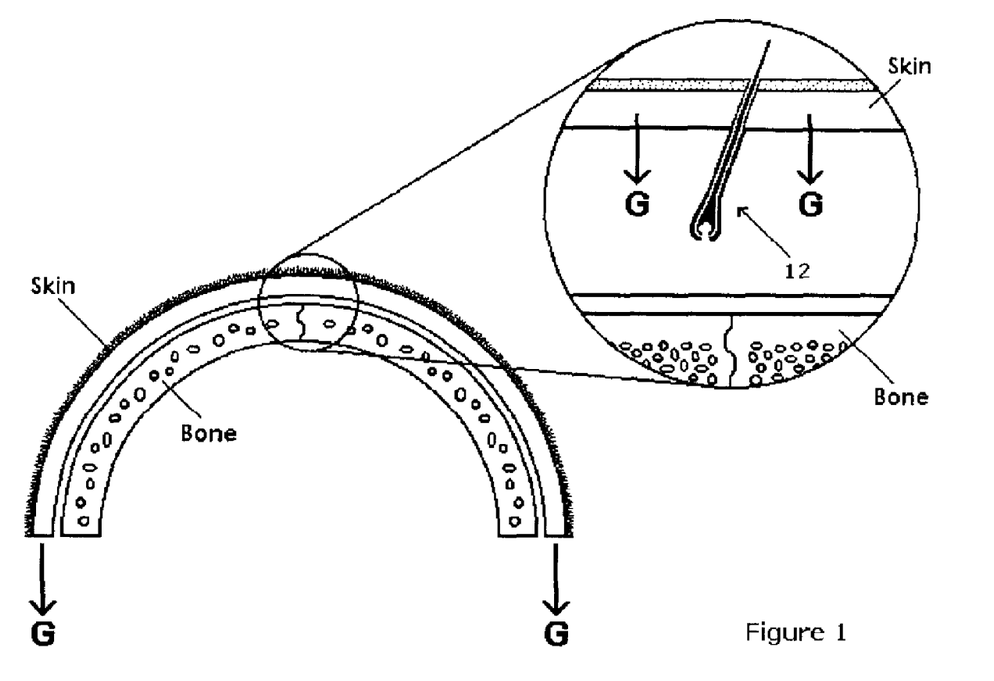
FIG. 1 is a diagrammatic representation showing the force of gravity compressing hair follicles between skin and bone.

I assert that the pressure caused by the force of gravity (i.e. the weight of the scalp) and applied on the hair follicles by the skin outside and the cranial bones inside is the cause of MPB. FIG. 1 shows gravity (G) acting on the skin relative to the bone on a persons head. The hair follicle 12 is subjected to the pressure by the skin due to gravity and the resisting force from the less malleable bone. Thinning of dermis and subcutaneous tissue with aging increases the pressure on the hair follicles 12, reducing the cushion (buffer) surrounding the hair follicles 12 as a person ages. Because of the anatomic structure of the cranium and the scalp, the pressure is highest at the vertex and at the right and left upper frontal regions. It decreases in the downward direction and has much less effect on the sides and back of the head.

By reducing the pressure on the hair follicles, MPB can be prevented or treated. Since the pressure on the hair follicles 12 increases continuously or regularly as the skin and subcutaneous tissues get thinner with advancing age, reducing the pressure may include at least keeping the pressure at the same level for a time period.

"Implant" should be understood as any device, tissue, cell, molecule or object that is introduced into a human body to function at least partially as a structural element at where it is introduced either temporarily or permanently using a surgical technique. To reduce the pressure on the hair follicles 12, one or more implants may be introduced below the surface of the skin. Any composition of matter may be used for the implant, such as any device, tissue, cell, molecule, or object. The implant functions at least partially as a structural element to either temporarily or permanently reduce the pressure for a given area. The implants reduce the pressure on the hair follicles 12 by at least partially assuming the pressure on itself, absorbing or otherwise dissipating the pressure, dispersing the pressure, transferring the pressure onto another structure or location, cushioning the hair follicles 12, segmenting (e.g., compartmentalizing) the scalp, suspending the scalp, combinations thereof, and/or other process. The implant cushions or buffers by intercepting or moderating the pressure.

The implant is delivered into a human body using surgical techniques. Surgical techniques include any surgical techniques starting from the simplest procedures, such as injection, to the most sophisticated surgeries, such as microsurgery or endoscopic surgery. If an agent that is delivered into a human body (e.g. injected into body) requires absorption to show its effects or to function, it is not an implant. Rather than treatment based on absorption, the implant at least partially acts as a structural element itself. The implant operates to relieve pressure on the follicles 12, at least partially, without a need for absorption. However, an implant may be absorbed eventually (i.e., absorbable), such as hyaluronic acid implant or an absorbable suture.

In order to increase the cushioning volume around the hair follicles 12, the implants may be tissues, cells, or molecules physically acting to reduce pressure. Such implants may include extra cellular matrix (ECM) molecules, such as hyaluronic acid (HA), elastin, their precursors, or like synthetic materials, such as hydrophilic polyacrylamide gel. ECM molecules provide most of the strength, elasticity, and compressibility of the skin. The predominant ECM molecules in the skin are collagen, elastin, proteoglycans (PGs) and glycosaminoglycans (GAGs). Collagen is the main structural protein. Elastin gives the resilience. GAGs, such as HA, are strongly hydrophilic and draw large amounts of water into their structure. GAGs are linked to core proteins and form proteoglycans. GAGs and PGs, therefore, play an important role in withstanding compression forces. In addition to the ECM molecules in the skin, subcutaneous fat buffers or cushions the roots of the hair follicles 12 in the scalp. These molecules, cells and/or tissues are introduced as implants, such as by injection.

Agents other than an implant may be used, such as other physical or chemical agents. These other agents may stimulate the cells that produce the ECM molecules to increase their production. Injection, topical or oral treatment by introduction of agents such as hyperbaric oxygen, vitamin C, electric current, heat, or electromagnetic radiation such as laser light is provided. The cells that produce the ECM molecules, such as fibroblasts, or the cells that cushion the hair follicles themselves, such as fat cells, may be stimulated to proliferate using agents such as basic fibroblast growth factor or epidermal growth factor. Fat cells may be stimulated to preserve their stored fat and/or deposit more fat using agents, such as neurotransmitters (e.g., acetylcholine or norepinephrine), receptor ligands (e.g., DHT receptors or angiotensin receptors), enzymes (e.g., aromatase or adenylate cyclase), hormones (e.g., estradiol or insulin), etc., or manipulating the agents' production or activity in the body. The cells that produce the ECM molecules or fat cells may be implanted. The cells that produce the ECM molecules or fat cells may be genetically modified or manipulated using microRNAs, small interfering RNAs, antisense oligonucleotides (DNA), viral or other transfection techniques. The physical or chemical agents may be effective on extra cellular molecules, on cell membrane molecules, on intrastoplasmic molecules, and/or on intranuclear molecules, including DNA and RNAs. These agents may be injected at the location of treatment or introduced orally or by topical application.

Figure 2A:
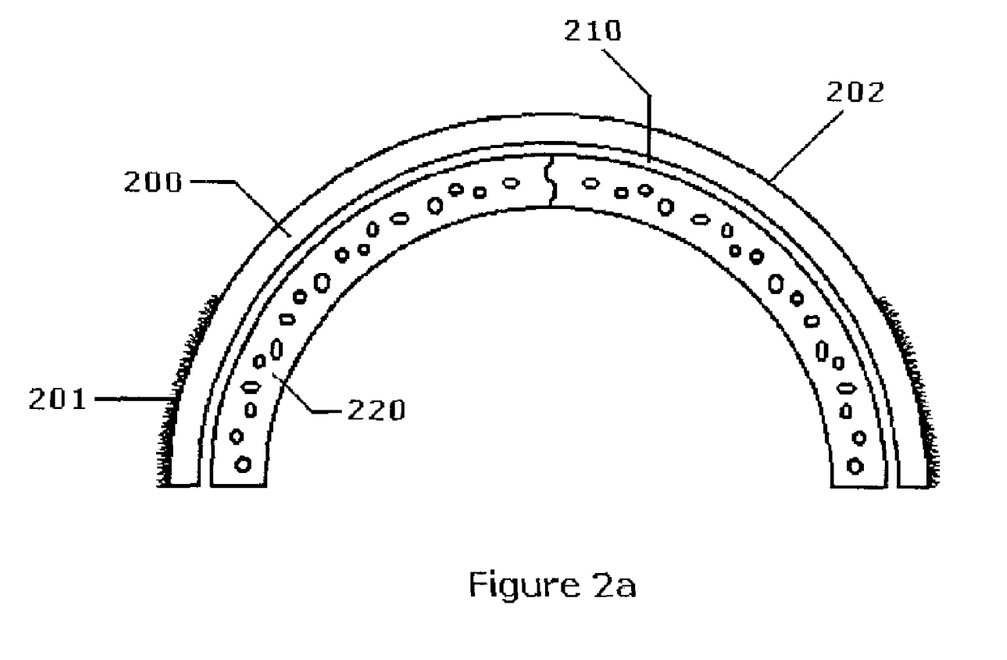
FIG. 2a is a diagram of a coronal cross section of scalp and underlying calvarium.

FIG. 2a shows a schematic representation of a coronal cross section of scalp and the underlying cranium 220. The scalp includes the tissues that overlie the cranial bones. From outside to inside, these tissues are the skin, connective tissue, aponeurosis or galea aponeurotica, loose areolar tissue, and the periosteum of the cranial bones (i.e., pericranium). The first letters of the names of these tissues make the word "scalp," but the usage of scalp may be a subset of this tissues. In FIG. 2a, the skin, connective tissue, and aponeurosis are shown together as one composite layer 200. This composite layer 200 is also referred to as scalp in this document. Scalp denotes all the tissues that form the scalp or a subset of these tissues. The galea is densely connected to the skin. The loose areolar tissue 210 is between the galea and the pericranium. The loose areolar tissue 210 allows the scalp move over the pericranium. The pericranium, not shown, is a thin membrane on the cranial bones 220. In downward direction, the galea is continuous with the superficial muscular aponeurotic system (SMAS). The galea becomes frontalis muscle at the front of the head and occipitalis muscle at the back of the head. In the temporal region, the galea is named superficial temporal fascia. Galea may be understood as the galea itself and also extensions depending on the location. In MPB, the balding skin 202 is typically located at the top of the head and non-balding skin 201 is located on the sides and back of the head. The pattern of MPB conforms to a pressure map of the scalp.

Figure 2B:
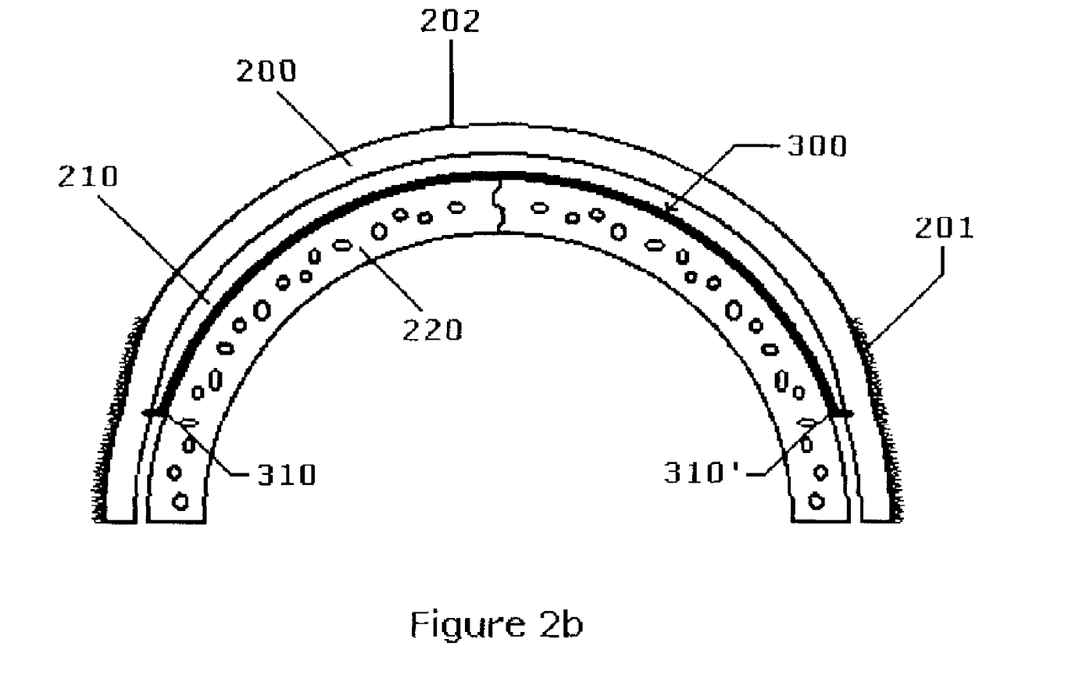
FIG. 2b is a diagram of the coronal cross-section of FIG. 2a with a sling-type implant.

The implant may be a device or object, such as with a connection portion and a support portion. FIG. 2b shows a sling-type implant 300 placed in the loose areolar tissue 210. The implant 300 is made of any biocompatible material strong enough to withstand the pressure assumed to reduce pressure on the follicles 12. For example, the implant 300 is polypropylene, polyester, polyurethane, nylon, expanded polytetrafluoroethylene (ePTFE), silicone, stainless steel, titanium, or other now known or later developed implant materials. Combinations of materials may be used. The sling-type implant 300 is preferably a uniform material, but may be coated with materials like polyurethane, titanium, or polyethylene vinyl acetate (PEVA). The surface of the implant 300 can be textured or smooth. The implant 300 is alternatively made of a tissue or tissues such as dermis, fascia, or tendon, which can be autogenic, allogenic, xenogenic or artificial.

The sling-type implant 300 is one or a combination of various shapes. For example, the implant 300 has an "I" shape with two endpoints. "V" shaped with three end points, "H" or "X" shaped with four end points, pound sign shaped with eight end points, ellipse shaped with multiple end points, irregular, "U" shape or other shapes may be used. The sling-type implant 300 may have planar regions, such as having a same shape and size as the current and/or potential hair loss area of the person who is going to receive the implant 300. The implant has a flat cross section, but a round, cubic, or other shape of cross section may be used. The sling-type implant 300 is of any thickness, such as paper-thin or several millimeters thick. The thickness may depend on the tensile strength of the material, the shape or distribution of the implant in the scalp, and/or the pressure load. The thickness of the implant may be tapered at the edges.

In one embodiment, the sling-type implant 300 is a surgical suture or other long, thin device. For example, surgical sutures may be used to act as an I, V, H, X, pound sign, or other shaped implant corresponding to one or more linear portions. A combination of non-suture implant and sutures may be used.

Referring to FIG. 2b, the ends 310, 310' of the sling-type implant 300 are attached to the galea. The ends 310, 310' are a portion of the implant 300 for connection. Any angle of the ends 310, 310' to the rest of the implant 300 may be used if the implant is not flexible. The length of the implant 300 is slightly shorter than the length of the scalp 200 that the implant 300 spans. The length is set so that the implant 300 does not compress the scalp 200. The sling-type implant 300 assumes the pressure created by the weight of the scalp 200 beyond its attachment ends 310, 310' to the galea. The portion of the implant 300 assuming the pressure is the support portion. The connection portion may also assume pressure since the connection portion is structurally connected to the support portion and/or by also suspending the scalp. In this way, the sling-type implant 300 segments the scalp 200 and suspends portions of the scalp 200. The implant 300 may be attached to the galea at more than two points along the length of the implant 300 to further segment the scalp and suspend each segment individually. Consequently, the pressure can be reduced further. The implant 300 can also be attached to the underlying pericranium or bone to prevent implant migration.

Figure 2C:
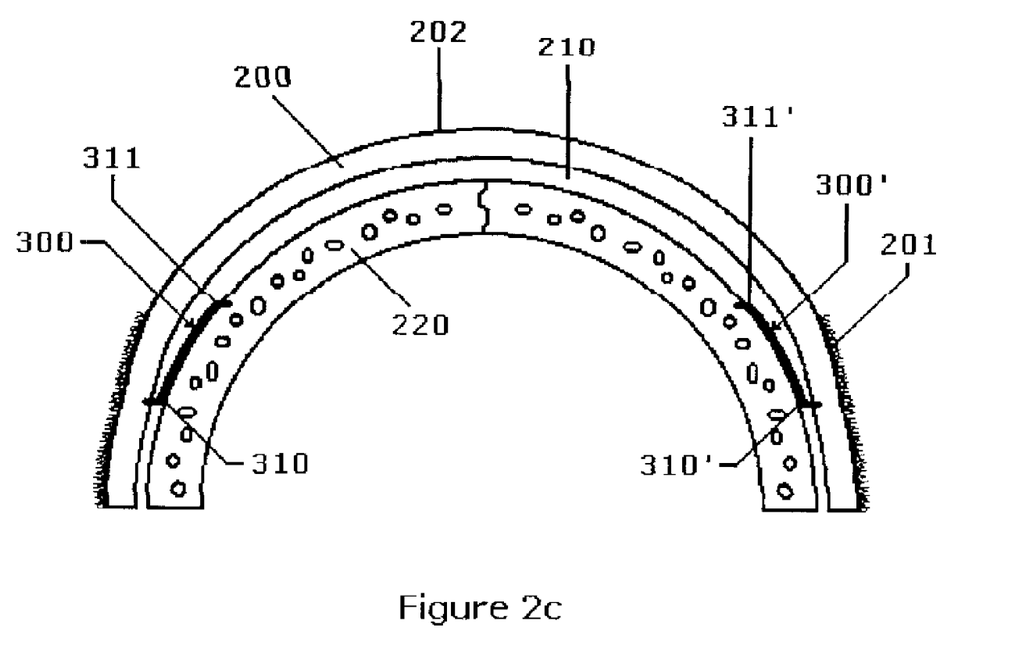
FIG. 2c is a diagram of the coronal cross-section of FIG. 2a with another sling-type implant.

FIG. 2c shows another embodiment of the sling-type implant 300, 300'. The scalp 200 is hung above the pericranium or bone separately on each side using a shorter implant 300, 300'. One end 310, 310' of the implants 300, 300' is attached to the underside of the galea and the other end 311, 311' is attached to the pericranium or bone at a point higher than the corresponding galea attachment point. Other arrangements and attachments may be used. The length of the implant 300, 300' is chosen to allow a desired amount of scalp mobility, such as being 5 to 10 millimeters depending on the location. Additional implants 300 may be provided. Depending on the size and the place of the balding area, the scalp 200 may be suspended at more than two points around the head.

Figure 3:
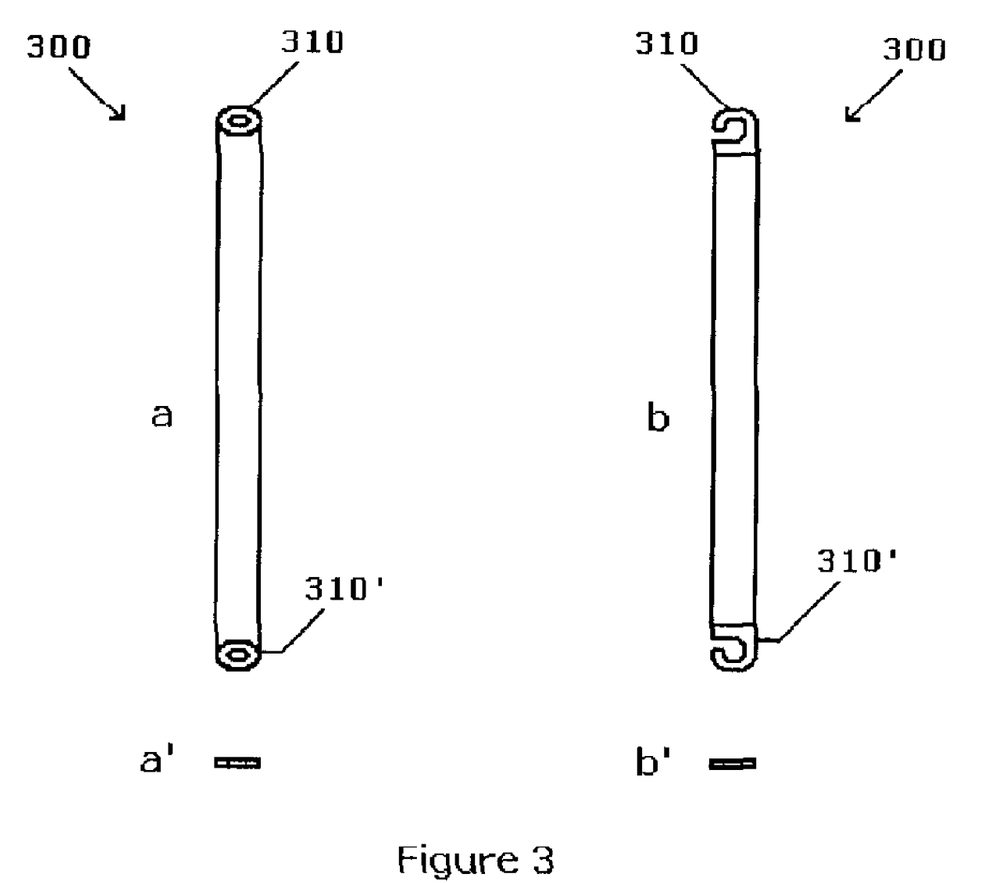
FIG. 3 shows a diagrammatic top view of a sling-type implant (a) with holes for sutures, (b) with hooks at both ends for tissue attachment, and respective side views (a') and (b')

FIG. 3 shows two further embodiments of sling-type implants 300. The attachment sites are at two ends 310, 310' of the implants 300. In one embodiment (b), hooks are provided for attachment. In another embodiment (a), holes are provided for suture attachment. There can be other attachment points along their length for additional galea and other attachments. Attachment is performed by suturing or hooking the implants to tissue. Other methods or materials may secure the implants 300, such as staples, clips, or bone anchors.

Figure 2D:
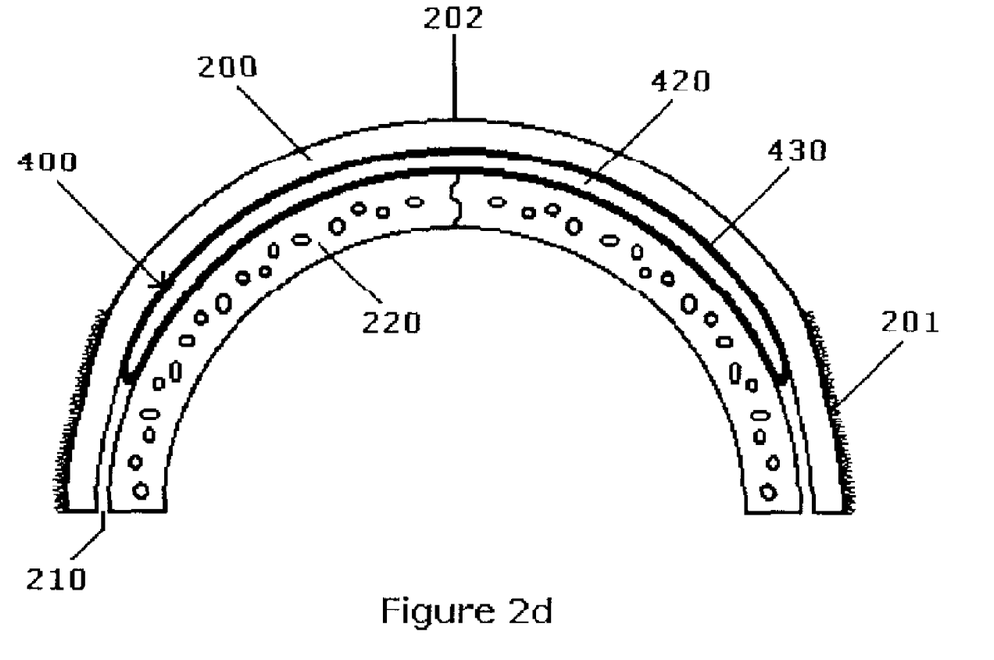
FIG. 2d is a diagram of the coronal cross-section of FIG. 2a with a cushion-type implant.

FIG. 2d shows another embodiment of a device or object implant 400. The implant 400 acts as a cushion. The cushion-type implant 400 is preferably placed in the lose areolar tissue 210.

The cushion-type implant 400 has only one cell (i.e., interior compartment) or more than one cell. If there are multiple cells, the cells may be open (i.e. able to communicate with each other and/or with the medium in which they are enclosed) or closed. The cells may be floating in a gas, liquid or gel medium. Any shape, size, or distribution of one or more cushion-type implants 400 may be provided. In one embodiment, a single cushion-type implant 400 or joined cushion-type implants 400 are sized to cover all, most, or substantially all current and/or potential balding skin areas from the underside. The cushion-type implant 400 has any desired thickness, such as about 1-5 millimeters. Greater or lesser thickness or a thickness that varies by location may be provided. Different thicknesses may be used for different people, depending on the skin and subcutaneous tissue thicknesses and the shape of the cranium. The thickness of the implant may be tapered at the edges. The cushion-type implant 400 may have an adjustable or fixed volume.

The cushion-type implant 400 is soft, such as soft as living human fat tissue. The interior 420 of the implant 400 is one or more of a gas (e.g., air), liquid (e.g., saline, or soybean oil), gel (e.g., hydrogel, or silicone gel), or soft solid (e.g., silicone elastomer or soft ePTFE). The shell 430 of the implant 400 is made of one or more flexible biocompatible materials, such as silicone elastomer or polypropylene. The interior 420 is softer or more malleable than the shell 430, but the shell 430 may be as soft as or softer than the interior 420. The cushion-type implant 400 may be coated with a material, such as polyurethane, titanium, or polyethylene vinyl acetate (PEVA). The surface of the cushion-type implant 400 may be textured or smooth. In other embodiments, the cushion-type implant is a uniform material without cells or the interior 420. The cushion-type implant 400 may have both viscous and elastic properties. In one embodiment, the implant 400 is a tissue or tissues, such as dermis or fat and fascia. The tissue may be autogenic, allogenic, xenogenic, or artificial. The tissue or tissues can be transferred to the scalp as grafts or flaps using surgery techniques, such as reconstructive surgery and microsurgery techniques.

Figure 4:
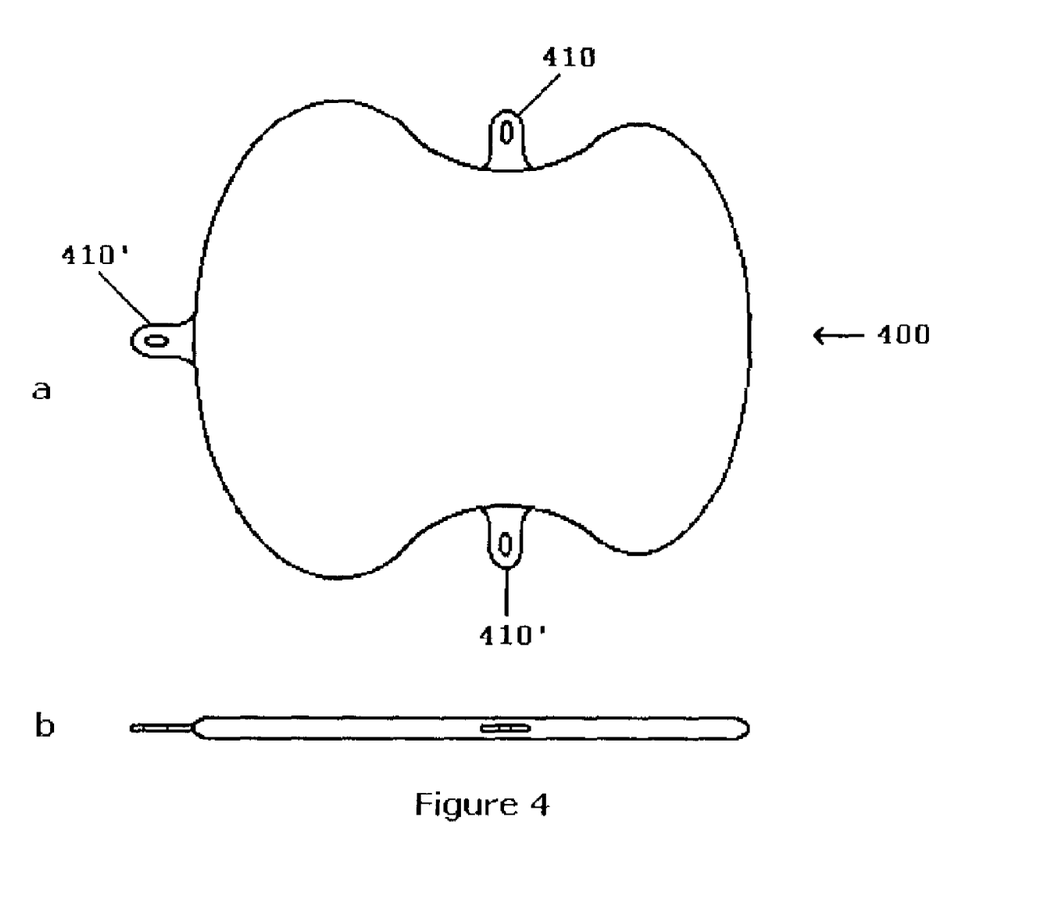
FIG. 4 shows diagrammatic top and side views of a cushion-type implant.

FIG. 4 shows tissue attachment sites 410, 410' on edges in one embodiment of a cushion-type implant 400. In other embodiments, one, more or all of the sites 410, 410' are not on edges. Each tissue attachment site is a hole for suturing, a tab for bonding, or other tissue connection device (e.g., tab for anchoring). A cushion-type implant 400 may have no tissue attachment sites 410, 410', such as where the implant 400 may be bonded, sutured or otherwise attached. A cushion-type implant may need attachment only to the underlying immobile tissues for prevention of implant migration. In one embodiment, the implant 400 is attached to underlying immobile tissues for prevention of implant migration.

Figure 2E:
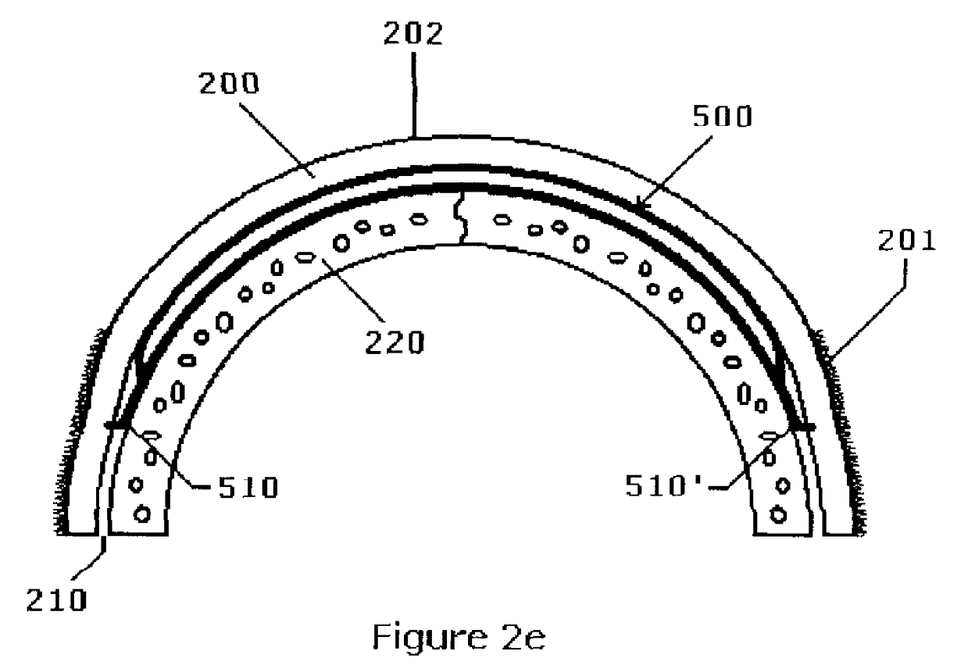
FIG. 2e is a diagram of the coronal cross-section of FIG. 2a with a mixed-type implant inserted into the loose areolar tissue beneath the galea aponeurotica.
Figure 5:
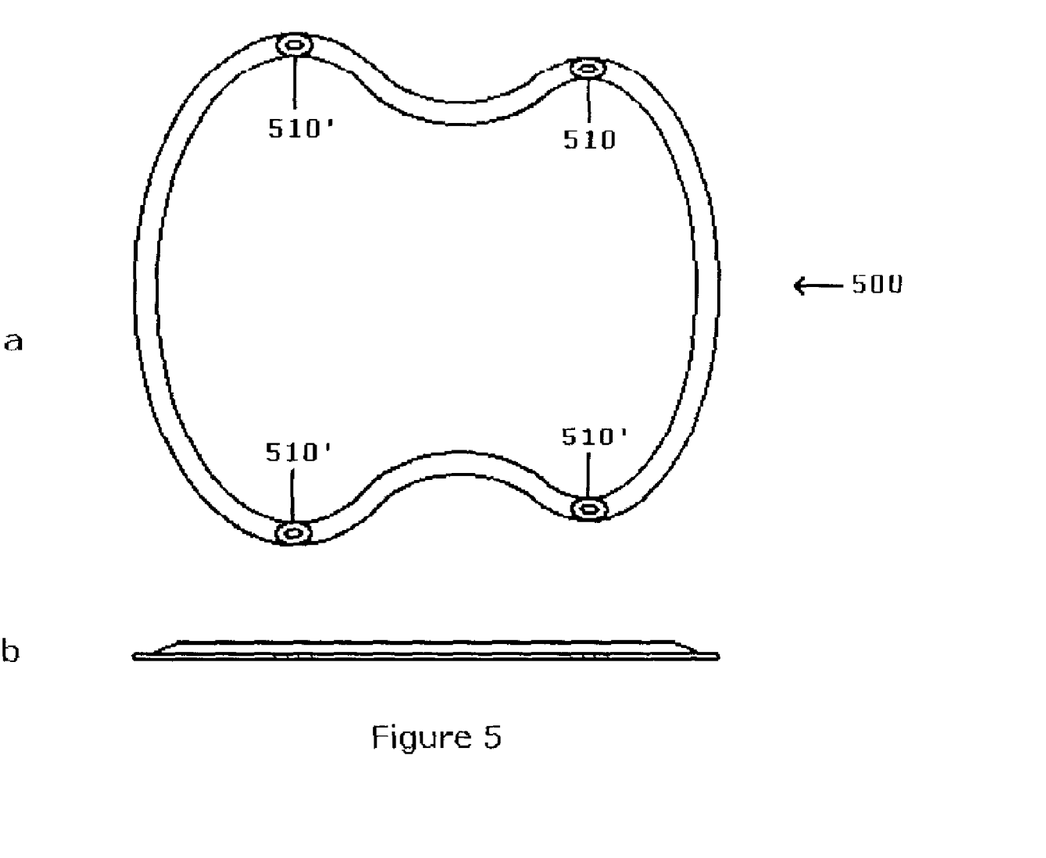
FIG. 5 shows diagrammatic top and side views of a mixed-type implant.

FIG. 2e shows a preferred mixed-type implant 500 inserted into the loose areolar tissue 210. The implant 500 is a combination of sling- and cushion-type implant with features of both implants 300 and 400. FIG. 5 shows another embodiment of the mixed-type implant 500. The same or different materials, sizes, and/or shapes as discussed above for cushion-type and sling-type implants 400, 300 can be used. The ratio of cushion to sling and relative locations may be varied. As shown, the sling is provided on the edges and the underside with a cushion in the center. The mixed-type implant 500 attaches to the galea through attachment sites 510, 510' like the sling-type implant 300. The sling portions segment and suspend the scalp 200 and the cushion portions cushion the overlying segment of the scalp 200. The cushion portions are soft, but the sling portions are hard enough to suspend the portion of the scalp 200.

The surgical operation for introduction and placement of an implant can vary depending on what the implant is and the preferences of the performer. A simple injection may be used, such as where the implant is an ECM molecule, cells or other injectable material. The implant may stay where injected if injected in appropriate locations. The density of the implant versus the density of the tissue, type of tissue, tissue boundaries, tissue compartments, size of the particles of the implants, cohesiveness of the implant molecules, or other properties may act to hold the implants in place. Some implants may be infiltrated and/or encapsulated or fixed otherwise by the cells or tissues of the host. Surgical operations other than injections may be used, such as free flap surgery (e.g., free omentum, dermofat or fasciofat flap transfers). A sling-type, a cushion type, or a mixed-type implant can be implanted under general or local anesthesia using one or more small incisions. Employing endoscopic surgery may reduce the number of incisions. The incision or incisions are placed away from the axial vessels of the scalp, and made taking the direction of the hair follicles into account so as not to cut through the follicles. The galea may be incised too. Creating a pocket for the implant in the loose areolar tissue under the galea may be easier than creating the same pocket over the galea. Over galea implantation may also be used.

After hemostasis, the implant is introduced into the pocket. The implant is positioned at the desired location. Depending on the type of the implant, the implant is attached to the overlying galea and to the underlying periosteum and/or bone using proper materials such as sutures, staplers, clips, anchors, combinations thereof, or other techniques. Attachment to just the galea or just the periosteum or bone may be used. For a mixed type implant, the galea attachment sites on the contralateral side are determined so that only enough slack of scalp to comfortably accommodate the implant is created over the implant. The incision or incisions are closed. Using drains or application of any other procedure throughout the surgery is at the discretion and judgment of the performer.

Although, the loose areolar tissue 210 is the preferred location for some type of implants, other locations can be preferred for other implants. For example, subcutaneous tissue is the preferred location for some of the injectable implants, such as ECM molecules or cells. However, injections into this location are performed cautiously to avoid injecting more than the desired amount of implant and increasing the pressure in that compartment instead of helping reduce the pressure on the hair follicles 12.

Although some examples are given, the materials that can be used to make a sling-type, a cushion-type or a mixed-type implant as well as the injectable materials are not exhaustively listed here. Any now known or later developed materials for use within the human body capable of cushion or suspension support may be used.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

I claim:

1. A method for prevention or treatment of hair loss, the method comprising:
   implanting material in a scalp;
   positioning the material to reduce pressure on hair follicles; and
   reducing pressure on the hair follicles of the scalp with the material.

2. The method of claim 1 wherein implanting the material comprises implanting a cushion material, wherein positioning comprises positioning the material adjacent skin with reduced or no hair growth, and wherein reducing pressure comprises cushioning the hair follicles.

3. The method of claim 1 wherein positioning comprises positioning the material to suspend at least a portion of the scalp, and wherein reducing the pressure comprises suspending the portion of the scalp.

4. The method of claim 3 wherein suspending comprises suspending different segments of the scalp with the material.

5. The method of claim 1 wherein positioning comprises positioning the material to segment at least a portion of the scalp, and wherein reducing the pressure comprises segmenting the portion of the scalp.

6. The method of claim 1 wherein reducing the pressure comprises at least partially absorbing the pressure.

7. The method of claim 1 wherein reducing the pressure comprises at least partially dissipating the pressure.

8. The method of claim 1 wherein reducing the pressure comprises at least partially dispersing the pressure.

9. The method of claim 1 wherein reducing the pressure comprises at least partially assuming the pressure by the material.

10. The method of claim 1 wherein reducing the pressure comprises at least partially transferring the pressure to another point.

11. The method of claim 1 wherein reducing the pressure comprises at least partially transferring the pressure onto another structure.

12. The method of claim 1 wherein implanting comprises injecting tissue, cells, molecules, or combinations thereof.

13. The method of claim 1 wherein implanting comprises surgically cutting the scalp.

14. The method of claim 13 wherein cutting comprises open surgery.

15. The method of claim 13 wherein cutting comprises minimally invasive surgery.

16. The method of claim 1 wherein implanting and positioning comprises:
   inserting a device into loose areolar tissue under a galea; and
   attaching the device to the galea.

17. The method of claim 16 further comprising:
   attaching the device to the underlying immobile tissues before or after attaching the device to the galea.

18. The method of claim 17 wherein the device is a surgical suture and attaching comprises suturing the galea to the underlying immobile tissues at least at one location.

19. A method for prevention or treatment of hair loss, the method comprising:
   obtaining a composition of matter; and
   inserting the composition of matter adjacent to hair follicles in a scalp at a position using a surgical technique, the position and the structure of the composition of matter configured to reduce pressure on the hair follicles.

20. The method of claim 19 wherein obtaining comprises obtaining tissue, cell, molecule, or combination thereof, and wherein inserting comprises injecting the tissue, cell, molecule or combination thereof directly at the position.

21. The method of claim 19 wherein obtaining comprises obtaining a cushion, and wherein inserting comprises positioning the cushion between the hair follicles and bone.

22. The method of claim 19 wherein the matter is operable to raise tissue including the hair follicles away from bone.

23. The method of claim 19 wherein inserting comprises attaching at least one suture to reduce pressure on the hair follicles.

24. The method of claim 19 wherein inserting comprises inserting under a galea.

* * * * *